US008846665B2

United States Patent
El-Azab et al.

(10) Patent No.: US 8,846,665 B2
(45) Date of Patent: *Sep. 30, 2014

(54) 6,7-DIHYDRO-[1,3,4]THIADIAZOLO-3,2-A][1,3]DIAZEPIN DERIVATIVE AND PHARMACEUTICAL COMPOSITION CONTAINING THE SAME AS NEUROMUSCULAR BLOCKER OR SKELETAL MUSCLE RELAXANT, AND METHOD FOR THE PREPARATION

(75) Inventors: Adel S. El-Azab, Riyadh (SA); Hussein I. El-Subbagh, Riyadh (SA); Khalid A. Al-Rashood, Riyadh (SA); Kamal E. H. El-Taher, Riyadh (SA); Mohamed A. Al-Omar, Riyadh (SA); Ghada S. Hassan, Riyadh (SA); Fatmah A. Al-Omary, Riyadh (SA); Alaa A. -M. Abdelaziz, Riyadh (SA); Mohamed M. Hefnawy, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 14/043,401

(22) PCT Filed: Apr. 11, 2012

(86) PCT No.: PCT/EP2012/001573
§ 371 (c)(1),
(2), (4) Date: Dec. 6, 2013

(87) PCT Pub. No.: WO2012/136385
PCT Pub. Date: Oct. 11, 2012

(65) Prior Publication Data
US 2014/0088091 A1    Mar. 27, 2014

(30) Foreign Application Priority Data
Apr. 8, 2011   (EP) ..................................... 11161597

(51) Int. Cl.
*A61K 31/55* (2006.01)
*C07D 513/04* (2006.01)

(52) U.S. Cl.
CPC ................................... *C07D 513/04* (2013.01)
USPC .......................................................... 514/221

(58) Field of Classification Search
CPC ... C07D 513/04; A61K 31/381; A61K 31/551
USPC .......................................................... 514/221
See application file for complete search history.

(56) References Cited

U.S. PATENT DOCUMENTS

| 4,352,816 A | 10/1982 | Hunkeler et al. |
| 4,382,032 A | 5/1983 | Hunkeler et al. |
| 4,405,517 A | 9/1983 | Hunkeler et al. |
| 4,407,752 A | 10/1983 | Hunkeler et al. |

FOREIGN PATENT DOCUMENTS

| DE | 10320732 A1 | 12/2004 |
| EP | 0 059 387 A2 | 9/1982 |

OTHER PUBLICATIONS

Pollard: "Neuromuscular Blocking Agents and Reversal Agents", Anaesthesia & Intensive Care Medicine, vol. 6, No. 6, Jun. 1, 2005, pp. 189-192, XP025344440, the whole document.
Arias: "Binding Sites for Exogenous and Endogenous Non-Competitive Inhibitors of the Nicotinic Acetylcholine Receptor", Biochimica et Biophysica Acta, vol. 1376, No, 2, Aug. 21, 1998, pp. 173-220, XP004281725, the whole document.

*Primary Examiner* — San-Ming Hui
(74) *Attorney, Agent, or Firm* — Lucas & Mercanti, LLP

(57) ABSTRACT

The present invention relates to a compound of formula 1 and addition salts thereof, a pharmaceutical composition containing the compound, a method for its preparation as well as the use of the compound as neuro-muscular blocker or skeletal muscle relaxant;

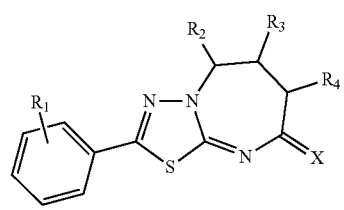

wherein each symbol is as defined in the Specification.

14 Claims, No Drawings

6,7-DIHYDRO-[1,3,4]THIADIAZOLO-3,2-A][1,3]DIAZEPIN DERIVATIVE AND PHARMACEUTICAL COMPOSITION CONTAINING THE SAME AS NEUROMUSCULAR BLOCKER OR SKELETAL MUSCLE RELAXANT, AND METHOD FOR THE PREPARATION

The present invention relates to compounds useful as neuromuscular blocker or skeletal muscle relaxant, pharmaceutical compositions containing the compound as well as a method for the preparation.

Neuromuscular blockade and anaesthesia are essential for surgical procedures. Muscle relaxation is required for the ease of surgical operations. The use of neuromuscular blockers or skeletal muscle relaxants will decrease the doses of the general anaesthetics required to induce consciousness in addition to muscle relaxation. Beside their adjunct use in anaesthesia, neuromuscular blockers are used in hospitals to ease tracheal intubation of the patients and to suppress the patient's spontaneous breathing. Other uses of skeletal muscle relaxants include prevention of fractures during electroshock therapy, suppression of titanic convulsions and diagnosis of myasthenia gravis. The medical history of these useful drugs dates back to the introduction of curare, the alkaloidal extract of *Chardrodendron tomentosum*. This was followed by the introduction of Gallamine, Succinylcholine (suxa-methonium), Pancuronium, Alcuronium and Atracurium (Singh, M. et al, *J. Chem. Pharm. Res.* 2010, 2, 264-273).

Neuromuscular blockers can be classified according to their mechanism of action into competitive neuromuscular blockers and depolarizing blockers. Most of the agents currently in use are of the competitive type. Competitive neuromuscular blockers block the nicotinic receptors located postsynaptic on skeletal muscle membranes. They compete with acetylcholine (ACh) for these receptors and prevent its action on evoking muscular contraction and thus muscle relaxation ensues gradually. Competitive neuromuscular blockers include d-Tubocurarine, Gallamine, Atracurium, Pancuronium, Vercuronium, Mevacurium and others. The depolarizing blockers mimic ACh in their ability to activate the postsynaptic nicotinic receptors on the skeletal muscles but differ from ACh in their ability to induce persistent depolarization of the skeletal muscles rendering them insensitive to any released ACh. The classical example of these drugs is Decamethonium which is not used in medicine now due to its prolonged action and the absence of a substance to reverse its action following operations. The only drug of this group that is still in use is Succinylcholine (Suxamethonium) due to its rapid action and short duration (up to 5 minutes following bolus injections at 0.5-2 mg/kg i.v.). Neuromuscular blockers can be classified according to onset of action and duration time into: ultra-short acting with onset within a minute following bolus i.v. administration and duration of 5 minutes e.g. Succinylcholine, and Gantacurium (Bigham, E. et al, US Patent 2001, U.S. Pat. No. 4,179,507); short acting with onset within 2 minutes and duration up to 20 minutes e.g. Mevacurium and Rocuronium; intermediate acting with onset within 5 minutes and duration up to 60 minutes e.g. Atracurium, Pancuronium, Vercuronium, Cisatracurium; long acting with onset up to 6 minutes and duration 75-100 minutes e.g. Pipercuronium and Doxacurium (Hunter, J. *New Engl. J. Med.* 1995, 332, 1691-1699; Omoigui E. The Anethesia Drugs Hand Book. 1995, Mosby, St. Louis, Mo., USA).

The competitive neuromuscular blockers are mostly used in medicine due to their antagonism by anticholinesterases e.g. Neostigmine, Pyridostigmine or Edrophonium following the end of the surgical operations or tracheal intubations. However, those suffer from various side effects e.g. apneas and even non-neuromuscular blockade induced side effects. These include release of histamine with consequent hypotension, broncho-constriction and excessive mucus secretions, headache as observed with Atracurium, d-Tubocurarine, and Mevacurium, (Basta, S. et al, *Br. J. Anaesth.* 1983, 55, 1055-106S; El Bradie, S. J. *Egypt Natl. Canc. Inst.* 2004, 16, 107-113; Jooste, E. et al, *Anesthesiology* 2007, 106, 763-772), blockade of muscarinic $M_2$ cardiac receptors and parasympathetic ganglia with the ultimate induction of tachycardia and elevation of the arterial blood pressure as observed with Gallamine (Bigham, E. et al, US Patent 2001, U.S. Pat. No. 4,179,507), stimulation of sympathetic autonomic ganglia, induction of tachycardia, elevation of the arterial pressure, increase in the intraocular pressure and induction of hyperkalemia as observed with Succinylcholine (Hunter, J. *New Engl. J. Med.* 1995, 332, 1691-1699; Bigham, E. et al, US Patent 2001, U.S. Pat. No. 4,179,507). An ideal neuromuscular blocker should possess a rapid onset of action, reasonable duration, and rapid reversibility after ending its use together with freedom from non-neuromuscular blockade side effects.

Neuromuscular blockers are, for example, also known from DE 103 20 732 which are based on thiazolo-[3,2-a][1,3]diazepin derivatives.

It is an object of the present invention to provide a neuromuscular blocker or skeletal muscle relaxant which overcomes the drawbacks of the prior art. Especially a compound shall be provided showing a competitive neuromuscular blocking activity, with reasonable onset of action and intermediate duration which can be rapidly reversed by anticholinesterases. Additionally, a pharmaceutical composition containing such an agent shall be provided, as well as a method for its preparation.

The objects are achieved by the features of the independent claims. Preferred embodiments are disclosed in the subclaims.

The term "alkyl" with regard to the definition of $R_1$-$R_4$ in the compound according to formula 1 is to be understood to comprise linear and branched alkyls. The term "halo" shall comprise derivatives which are mono-, di-, tri- or poly-halo-substituted.

If possible, all substituents $R_1$-$R_4$ may be optionally further substituted, for example by halogen, amino, substituted amino, $C_1$-$C_{20}$-alkyl, $C_1$-$C_{20}$-haloalkyl, $C_1$-$C_{20}$-alkoxy or $C_1$-$C_{20}$-haloalkoxy, or mercapto, alkylthio, alkylamino, arylthio, heteroarylthio, arylamino or heteroarylamino.

In one embodiment, at least two substituents $R_1$-$R_4$, preferably $R_3$ and $R_4$ may be taken together to form an, optionally substituted, alicyclic, aryl or heteroaryl ring system.

Surprisingly, it was found that the compounds as proposed in the present invention overcome many of the disadvantages and problems that are usually accompanied with neuromuscular blockers known in the art. Especially the compounds of the present invention show a comparable competitive neuromuscular blocking activity, with reasonable onset of action. Also, intermediate duration which can be rapidly reversed by anticholinesterases is acceptable.

1,3,4-Thiadiazolo[3,2-a][1,3]diazepine analogs could be obtained adopting published methods (Molina, P. et al, *J. Org. Chem.* 1993, 58, 5264-5270; Imming, P. et al, *Arch. Pharm.* (Wienheim) 1995, 238, 207-215). The compounds of invention and their analogs (1) are synthesized according to an inventive method, Scheme 1.

Scheme 1

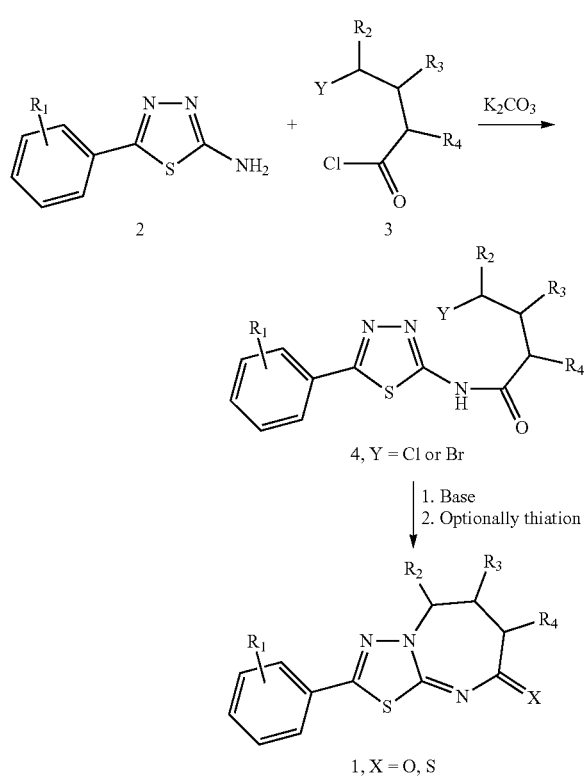

The proper 2-amino-5-substituted-1,3,4-thiadiazole (2) were acylated with the suitable acid chloride derivatives (3), where Y is chlorine or bromine, preferably bromine, and anhydrous potassium carbonate in a suitable solvent, such as, for example, toluene, ethylbenzene, o-, m-, and p-xylene, octane, nonane and isopropylbenzene, preferably toluene and ethylbenzene at temperature ranging from about 100° to 150° C., preferably 100-120° C. The products 4 can be purified by silica gel and neutral alumina chromatography. Compounds of the formula 4 were cyclized using secondary amines, such as for example, diethylamine, pyrrolidine, morpholine, piperidine, N-methylpiperazine, preferably pyrrolidine and piperidine, in a suitable solvent, such as for example toluene, ethylbenzene, o-, m-, and p-xylene, isopropylbenzene, preferably toluene, o-xylene at temperature ranging 100-180° C., preferably 120-130° C. The products of the formula 1 were obtained and purified using either silica gel or alumina column chromatography. Compounds of formula 1 can be optionally thiated in using conventional thiating agents, for example, Lawesson-reagent, according to report methods, such as Nishio T. et al., *Tetrahedron* 1999, 55, 5017-5026; Swanson D. M. et al., *Eur. J. Med. Chem.* 2009, 44, 4413-4425.

Adult male Wistar rats (250 g) and 4-day old chicks (50 g) were used to conduct the neuromuscular blocking activity evaluation. They were housed in cages and kept at a temperature of 20±2° C. and a relative humidity of 55±5% with a light-dark cycle of 12 h. The animals were provided with Purina rodent's chow pellets supplied by Grain silos and Flour Mills Organization, Riyadh, Saudi Arabia and had both food and water ad libitum. The chicks were bought from the local market in Riyadh. Male Wistar rats (250 g) were randomly divided into various groups (N=4-8 animals). The animals were prepared following modifications of the reported method (Henning, R. *Br. J. Pharmacol.* 1993, 108, 717-720; Thesleff, S. et al, *J. Pharmacol. Expt. Ther.* 1954, 111, 99-118). Test drugs, standards or vehicles were administered intraperitoneal dissolved in dimethyl sulfoxide, or water as appropriate in various doses 1-100 mg/kg. In all experiments a control group was included and received intraperitoneal injections of the test compounds' vehicle. The $ED_{50}$ (Effective dose required to produce 50% reduction of the rat tibialis twitch) was calculated for each drug. Also the dose that produced 90% of twitches depression was calculated. The response of the muscle to titanic stimulation was tested before administration of any drug and following 90% inhibition of the twitches.

Administration of compounds of the formula 1 induced dose-dependent inhibitions of the twitches in rats i.e. neuromuscular blockade leads to skeletal muscle relaxation. The competitive neuromuscular blocker Atracurium and the depolarizing neuromuscular blocker Succinylcholine were used as positive controls. The $ED_{50}$ values, times for onset for 50% and 90% inhibitions, the effects of tetanus, the anticholinesterase—Physostigmine 100% reversal, and the duration of the blocks were recorded. The onset times of compounds of the formula 1 were ranged from 3-10 minutes. The $ED_{50}$ values were ranged from 0.15-0.36 mmoles/kg i.p. Representative example is shown in Example 3.

Intraperitoneal administration of compounds of the formula 1 in single doses ranged from of 0.15-0.3 mmoles/kg, induced flaccid paralysis of the chicks within 1-15 minutes. The paralysis started with head movement and drop; then complete flaccid paralysis occurred. The onset of head drops were ranged from 15 sec-11 minutes whereas the flaccid paralysis ranged from 1-15 minutes following administration. Atracurium and Succinylcholine were used as positive controls. The mechanism of action of compounds of the formula 1 was similar but with more rapid onset of action than that of Atracurium; and almost similar to that of Succinylcholine. Representative example is shown in Example 4.

Compounds of the invention (formula 1) showed neuromuscular blocking activity on rats and chicks. The results obtained on rats following tetanus application during compounds of invention induced neuromuscular blockade suggest that the compounds of formula 1 acted via competitive mechanism with ACh released following electrical stimulation of the sciatic nerve to the postsynaptic nicotinic receptors on the tibialis muscle membrane. Such a competitive mechanism is supported by the studies in chicks in which compounds of the invention induced head drop and flaccid paralysis of the limbs, by the use of reported techniques (Thesleff, S. et al, *J. Pharmacol. Expt. Ther.* 1954, 111, 99-118). The complete reversal of compounds of the formula 1 induced block by the anticholinesterase—physostigmine confirms their competitive mechanisms of action. Competitive blockers-induced blockade is usually reversed by various anticholinesterases such as Neostigmine, Edrophonium and Pyridostigmine (Henning, R. *Br. J. Pharmacol.* 1993, 108, 717-720; Sacan, O. et al, *Anesth. Analg.* 2007, 104, 569-574; Garg, R. et al, *J. Anesth.* 2008, 18, 1-5; Hunter, J. et al, *Br. J. Anaesth.* 2006, 97, 123-126). Regarding the onset of action and duration, the studies in rats and chicks revealed that compounds of the formula 1 possess onset of action more rapid than the well established competitive neuromuscular blocker-Atracurium. The duration of compounds of the formula 1-induced block is in the same range of the standard competitive neuromuscular blockers, such as Atracurium, Pancuronium, Veracuronium and Cisatracurium (Hunter, J.

New Engl. J. Med. 1995, 332, 1691-1699; Omoigui E. The Anethesia Drugs Hand Book. 1995, Mosby, St. Louis, Mo., USA).

The $LD_{50}$ values of compounds of formula 1 were performed. Compounds were given intraperitoneally in doses ranging from 0.1-5 mmole/kg. The animals were observed for up to 6 hours continuously and were then kept under observation for 72 hours. All behavioral changes and death during the observation periods were recorded. The percentage of death at each dose level was then calculated, and the $LD_{50}$ values were obtained (Ghosh, M., Fundamentals of Experimental Pharmacology, Scientific Book Agency, Calcutta. 1984, pp 153-158, 187-189). The Therapeutic Index of each compound was calculated following the determination of the effective neuromuscular blocking dose. Representative example is shown in Example 5.

The biological evaluation of the new compounds of the formula 1 of the invention revealed that the compounds are neuromuscular blockers which mark the era of the introduction of a new class of intermediate acting skeletal muscle relaxants. Compounds of this invention acted via competitive mechanism with ACh released which could be completely reversed by the anticholinesterase—Physostigmine. Therefore, compounds of the formula 1 of the invention have the potential use as muscle relaxants.

Compounds of the formula 1 of the invention, and their acid addition salts display neuromuscular blocking skeletal muscle relaxants activity. The present invention includes pharmaceutical formulations which, in addition to non-toxic, inert pharmaceutically suitable excipients, contain one or more active compounds according to the invention, or which consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, and ampoules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulations auxiliaries of every kind.

Tablets, dragees, capsules, pills, granules, solutions and sprays may be mentioned as preferred pharmaceutical formulations.

Tablets, dragees, capsules and pills can contain the active compound or compounds alongside the customary excipients, such as (a) fillers and extenders, for example starches, lactose, sucrose, glucose, mannitol and silica, (b) binders, for example carboxymethylcellulose, alginates, gelatin and polyvinylpyrrolidone, (c) humectants, for example agar-agar, calcium carbonate and sodium bicarbonate, (e) solution retarders, for example paraffin, and (f) resorption accelerators, for example quaternary ammonium compounds (g) wetting agents, for example cetyl alcohol and glycerol monostearate, (h) adsorbents for example kaolin and bentonite, and (i) lubricants, for example talc, calcium stearate and magnesium stearate and solid polyethylene glycols, or mixtures of the compounds listed under (a) to (i).

The tablets, dragees, capsules and pills can be provided with the customary coatings and shells, optionally containing pacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the above mentioned excipients could also be in a micro-encapsulate form.

Solutions and emulsions for parenteral administration can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cotton seed oil, groundnut oil, maize germ oil, olive oil, castor oil and sesame oil, glycerol, glycerol-formal, tetrahydrofurfuryl alcohol, polyethylene glycol and fatty acid esters of sorbitol, or mixtures of these substances, in a sterile form which is isotonic with blood.

The therapeutically active compounds should preferably be present in the above-mentioned pharmaceutical formulations in a concentration of about 0.1 to 99.5, preferably of about 0.5 to 95% by weight of the total mixture.

The above-mentioned pharmaceutical formulations can also contain other pharmaceutical formulations; can also contain other pharmaceutical active compounds in addition to the active compounds according to the invention.

The above-mentioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention in human and veterinary medicine.

The actual dosage unit will be determined by such generally recognized factors as body weight of the patient and/or severity and type of pathological condition the patient might be suffering. With these considerations in mind, the dosage unit for a particular patient can be readily determined by the medical practitioner in accordance with the techniques known in the medical arts.

The precise instructions for pharmaceutical administration of the compounds and agents according to the invention necessarily depend on the requirements of the individual case, the nature of treatment, and of course the opinion of the treating physician.

It will be understood by those skilled in the art that various modifications and substitutions may be made to the invention as described above without departing from the spirit and scope of the invention. Accordingly, it is understood that the present invention has been described by way of illustration and not limitation.

EXAMPLE 1

N-[5-(4-bromophenyl)-1,3,4-thiadiazol-2-yl]-4-chlorobutanamide

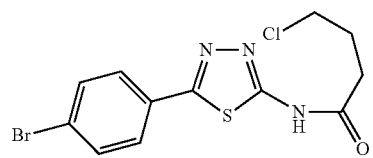 [SMILES: O=C(CCCCl)Nc1nnc(-c2ccc(Br)cc2)s1]

A mixture of 5-(4-bromophenyl)-1,3,4-thiadiazol-2-amine (10.2 g, 0.04 mol), 4-chlorobutyryl chloride (11.3 g, 9.0 ml, 0.08 mol) and potassium carbonate (5.5 g, 0.04 mole) in toluene (100 ml) was heated under reflux for 4 hr. The toluene was then evaporated under reduced pressure. The residue was then quenched with water, stirred, and filtered. The solid obtained was washed, dried and recrystallized from toluene to give the required product (12.5 g, 87% yield), mp 187-9° C., m/e 360, 15.7% (consistent with molecular formula $C_{12}H_{11}BrClN_3OS$, calcd. 360.66). $^1$H NMR (DMSO-$d_6$): δ 1.96-2.22 (m, 2H, —$CH_2$), 2.69-2.81 (m, 2H, —$CH_2$), 3.71-3.72 (m, 2H, —$CH_2$), 7.49-7.88 (dd, 4H, ArH), 12.76 (br s, 1H, NH). $^{13}$C NMR: δ 27.3, 32.1, 44.6, 123.8, 128.7, 129.4, 132.3, 158.5, 160.7, 170.7.

EXAMPLE 2

(E)-2-(4-bromophenyl)-6,7-dihydro-[1,3,4]thiadiazolo[3,2-a][1,3]diazepin-8(5H)-one (GS-53)

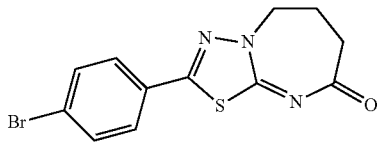 [SMILES: O=C1CCCN2N=C(c3ccc(Br)cc3)SC2=N1]

A mixture of N-[5-(4-bromophenyl)-1,3,4-thiadiazol-2-yl]-4-chlorobutan-amide (1.44 g, 0.004 mol) and piperidine (0.7 g, 0.8 ml, 0.008 mol) in toluene (50 ml) was heated under reflux for 3 h. The reaction mixture was cooled, poured into water and stirred. Toluene was separated dried and evaporated to give a crude product which was purified by repeated silica gel and neutral alumina column chromatography eluting with EtOAc/hexane (50:50 v/v) and $CHCl_3$/hexane (80:20 v/v); mp 204-7° C., m/e 324, 78% (consistent with molecular formula $C_{12}H_{10}BrN_3OS$, calcd. 324.20) $^1$H NMR $CDCl_3$): δ 2.32-2.40 (m, 2H, —$CH_2$), 2.76 (t, J=7.5 Hz, 2H, —$CH_2$), 4.29 (t, J=7.5 Hz, 2H, —$CH_2$), 7.62-7.84 (dd, J=8.5 Hz, 4H, ArH). $^{13}$C NMR: δ 18.3, 31.2, 47.9, 125.0, 128.7, 129.5, 132.3, 157.5, 162.9, 173.7.

The NMR spectral data assignments of compounds of Example 1 and Example 2 are based on analysis of the $^1$H, Attached Proton Test (APT), the Distortionless Enhancement Polarization Transfer (DEPT), correlated spectroscopy (COSY), Heteronuclear Multiple Quantum Coherence Spectroscopy (HMQC), NMR spectra for each compound.

EXAMPLE 3

Measurement of the Neuromuscular Blocking Activity of GS-53 in Rats

Male Wistar rats were prepared following modifications of the reported methods (Henning, R. *Br. J. Pharmacol.* 1993, 108, 717-720). The animals were anaesthetized using 25% urethane in water (w/v, 1.25 g/kg i.p). Each animal was laid on its back and fixed to a surgical board and body temperature was maintained by an over-head lamp. An incision was made on the neck, the trachea was located freed and a cannula was inserted to supply artificial ventilation with room air delivered by Parvalux Electric Motors Ltd rodents' respirator (Wallisdown, Bournermouth, England) at a frequency of 90 breaths per minute and a tidal volume of 20 c.c./kg. Furthermore, an incision was made to remove the skin covering the tibialis and its neighbor muscles on the right leg. The membrane covering the tibialis muscle was removed and its tendon freed from the Knob in the middle of the foot. The tendon was tied with a strong thread, passed through a bully, attached to a force displacement transducer (10-100 g, Narco-Biosystems, Myograph F 2000; USA) which was connected to a Narco Physiograph via Universal Coupler Type 7173. An incision was made on the lateral right side of the animal just above the site of the sciatic nerve supplying the tibialis muscle. The sciatic nerve was freed and the nerve was secured between a platinum electrodes. A strong tie was made on the portion of the nerve nearer to the spinal cord to prevent a generalized electrical stimulation. The electrodes were attached to an electric stimulator (Science and Research Instruments, Ltd, Kent, U.K.). Both of the muscle and the nerve were covered with paraffin oil at 37° C. to prevent dryness of the tissues. The Tibialis muscle twitches were induced using the following parameters: supramaximal voltage of 40 volts, at a frequency of 0.3 Hz and 0.5 msec duration. When tetanus was performed the frequency was increased to 30 Hz and the speed of recording was increased from 0.25 cm/sec to 1 cm/sec and stimulation was performed for 5-10 sec. The calibration system built in the transducer was used to measure the tension of the muscle. Changes in the muscle tension (twitches) were expressed as percentage change from the pre-drug values.

GS-53, standards or vehicles were administered intraperitoneally dissolved in dimethyl sulfoxide, or water as appropriate in various doses 1-100 mg/kg. The effect of each dose on the twitch response was calculated as a percentage of the pre-drug amplitude. The $ED_{50}$ was calculated for GS-53. Also the dose that produced 90% of twitches depression was calculated. The response of the muscle to titanic stimulation was tested before administration of GS-53 and following 90% inhibition of the twitches. To investigate the reversibility of any block, the anticholinesterase—Physostigmine was injected in a single bolus injection of 100 μg/kg. The onset time of reversal and the percentage of reversal were monitored and calculated, respectively. The duration of each block was monitored. In all animals rectal temperature was maintained at 37±1° C. The duration of action of GS-53 was 2.3 times that of Atracurium, and its blockade was completely reversed following administration of Physostigmine (Table 1).

TABLE 1

Summary of the Effects of GS-53, Atracurium and Succinylcholine on the rat tibialis electrically-induced twitches together with the effects of tetanus and physostigmine at a dose of 100 mg/kg i.p. (N = 4-8 animals).

| *Parameter | GS-53 | Atracurium | Succinylcholine |
|---|---|---|---|
| $ED_{50}$ (mmole/kg i.p.) | 0.15 (48.6 mg) | 0.016 | 0.03 |
| Time of onset of Block (min) | 3 ± 0.9 | 5 ± 0.8 | 2 ± 0.1 |
| Time of 50% Block (min) | 7 ± 0.6 | 8 ± 0.2 | 3 ± 0.1 |
| Time of 90% Block (min) | 10 ± 3 | 12 ± 1.3 | 5 ± 0.2 |
| Effect of Tetanus (30 Hz) | Non-Maintained | Non-Maintained | Well-Maintained |
| Effect of Physostigmine | 100% Reversal | 100% Reversal | No Reversal |
| Time of onset of Reversal (min) | 1.0 | 2.0 | — |
| Time for 100% Reversal (min) | 6 ± 1.2 | 3 ± 0.4 | — |

TABLE 1-continued

Summary of the Effects of GS-53, Atracurium and
Succinylcholine on the rat tibialis electrically-induced
twitches together with the effects of tetanus and physostigmine
at a dose of 100 mg/kg i.p. (N = 4-8 animals).

| *Parameter | GS-53 | Atracurium | Succinylcholine |
|---|---|---|---|
| Duration of the Block (min) | 70 ± 12 | 30 ± 6 | 20 ± 1.8 |

*The results reported were the mean ± S.E., N = number of animals used. Significant differences between the various treatments were performed using paired or un-paired t-test. P values < 0.05 were considered significant.

TABLE 2

Effects of GS-53, Atracurium and Succinyl choline in chicks

| Parameter | GS-53 | Atracurium | Succinyl choline |
|---|---|---|---|
| $ED_{50}$ (mmole/kg i.p.) | 0.15 (48.6 mg) | 0.016 | 0.03 |
| Onset of head drop (min) | 0.25 ± 0.1 | 5 ± 0.8 | — |
| Onset of muscle relaxation (min) | 1 ± 0.08 | 10 ± 0.8 | 0.5 ± 0.02 |
| Type of neuromuscular paralysis | Flaccid | Flaccid | Spastic |
| Mechanism of action | Competitive | Competitive | Depolarizing |

*The results reported were the mean ± S.E., N = number of animals used. Significant differences between the various treatments were performed using paired or un-paired t-test. P values < 0.05 were considered significant.

EXAMPLE 4

Measurement of the Neuromuscular Blocking Activity of GS-53 in Chicks

The effects of GS-53 and the standard drugs Succinylcholine and Atracurium were administered to 4-day old chicks to confirm the mode of the neuromuscular blockade (Buttle, G. et al, *J. Pharm. Pharmacol.* 1949, 1, 991-992; Thesleff, S. et al, *J. Pharmacol. Expt. Ther.* 1954, 111, 99-118; ELTahir, K. Guide to Drug Discovery, 2008, Riyadh, KSA). Sub-maximal dose of GS-53 and the standards as revealed in the rats studies were administered (i.p) to the chicks and the type of paralysis was noted. Intraperitoneal administration of GS-53 in single dose of 0.15 mmoles/kg, induced flaccid paralysis of the chicks within one minute. The paralysis started with head movement and drop; then complete flaccid paralysis occurred. The onset of head drop was 15 sec whereas the flaccid paralysis was one minute following administration. Atracurium and Succinylcholine were used as positive controls. The mechanism of action GS-53 seemed to be similar but with more rapid onset of action than that of Atracurium; and almost similar to that of Succinylcholine (Table 2).

EXAMPLE 5

Determination of the Lethal Dose ($LD_{50}$) of GS-53

Male mice were divided into various groups and GS-53 was administered in various doses ranging from 0.1-5 mmole/kg, intraperitoneal. Following treatments, the animals were observed for up to 6 hours continuously and were then kept under observation for 72 hours. All behavioral changes and death during the observation periods were recorded. The percentage of death at each dose level was then calculated, converted to probits and the $LD_{50}$ values were calculated as outlined by (Ghosh, M., Fundamentals of Experimental Pharmacology, Scientific Book Agency, Calcutta. 1984, pp 153-158, 187-189). the calculated $LD_{50}$ of (E)-2-(4-bromophenyl)-6,7-dihydro-[1,3,4]thiadiazolo[3,2-a][1,3]diazepin-8 (5H)-one (GS-53, Example 2) was found to be 195.0 mg/kg with 95% confidence limits of 185.25-204.75 mg/kg.

The features disclosed in the foregoing description and in the claims may, both separately and in any combination thereof, be material for realizing the invention in diverse forms thereto.

We claim:

1. A compound according to formula 1 or an addition salt thereof:

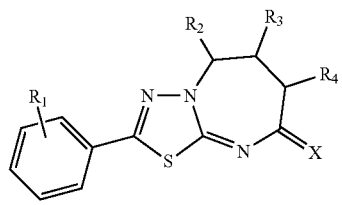

wherein $R_1$, $R_2$, $R_3$ and $R_4$ are each independently selected from hydrogen, halogen, $C_1$-$C_{20}$-alkyl, $C_1$-$C_{20}$-haloalkyl, $C_1$-$C_{20}$-alkoxy, $C_1$-$C_{20}$-haloalkoxy, aryl, heteroaryl, mercapto, alkylthio, amino, and alkylamino, or wherein $R_3$ and $R_4$ are alicyclic, aryl or heteroaryl ring systems, and are optionally substituted by halogen, amino, $C_1$-$C_{20}$-alkyl, $C_1$-$C_{20}$-haloalkyl, $C_1$-$C_{20}$-alkoxy, $C_1$-$C_{20}$-haloalkoxy, mercapto, alkylthio, alkylamino, arylthio, heteroarylthio, arylamino or heteroarylamino, and wherein X is O or S.

2. The compound according to claim 1, wherein $R_2$ is hydrogen, mercapto or $C_1$-$C_{20}$-alkyl.

3. The compound according to claim 2, wherein $R_3$ is hydrogen or is taken together with $R_4$ to form an alicyclic, aryl or heteroaryl ring system, which is optionally substituted by halogen, amino, $C_1$-$C_{20}$-alkoxy, $C_1$-$C_{20}$-haloalkoxy, mercapto, alkylthio, alkylamino, arylthio, heteroarylthio, arylamino or heteroarylamino.

4. The compound according to claim 1, wherein $R_1$, $R_2$, $R_3$ and $R_4$ are independently selected from aryl or heteroaryl.

5. The compound according to claim 4, wherein the compound is an addition salt of hydrochloride, hydrobromide, phosphate, nitrate, acetate, malate, succinate, fumarate, tartrate, salicylate, sorbate, lactate, p-toluene sulphate, or naphthalene-1,5-disulfonate.

6. A method for preparing the compound according to claim 1, comprising reacting a compound according to formula 2 with a compound according to formula 3 in the presence of $K_2CO_3$ to produce a compound according to formula 4, and then reacting the compound of formula 4 with, a secondary amine to produce the compound of formula 1, as depicted in scheme 1:

Scheme 1

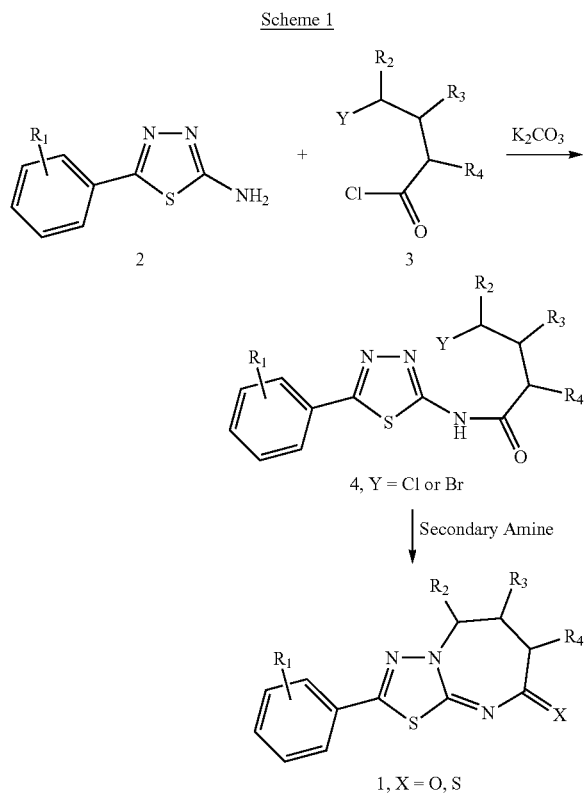

wherein Y is Cl or Br, X is O or S, and $R_1$ to $R_4$ are as defined in claim 1.

7. The method according to claim 6, wherein the reaction of compound 2 and compound 3 is in the presence of a solvent.

8. The method according to claim 7, wherein the reaction of compound 4 is a cyclization reaction with diethyl amine, pyrrolidine, morpholine, piperidine, N-methylpiperazine, in toluene, ethylbenzane, o-xylene, m-xylene, p-xylene, or isopropylbenzene.

9. A pharmaceutical composition comprising a compound according to claim 1 and a pharmaceutically acceptable carrier or excipient.

10. A method of blocking the neuromuscular system and relaxing skeletal muscles in a subject comprising administering an effective amount of the pharmaceutical composition according to claim 9 to the subject.

11. The compound of claim 3, wherein the compound is an addition salt of hydrochloride, hydrobromide, phosphate, nitrate, acetate, malate, succinate, fumarate, tartrate, salicylate, sorbate, lactate, p-toluene sulphate, or naphthalene-1,5-disulfonate.

12. The compound of claim 5, wherein $R_1$, $R_2$, $R_3$ and $R_4$ are independently selected from phenyl, naphthyl, furyl, pyrrolyl, thienyl, imidazolyl, thiadiazolyl, pyridinyl, pyridazinyl, pyrimidinyl, benzothiazolyl and oxadiazolyl.

13. The pharmaceutical composition of claim 9, wherein $R_1$, $R_2$, $R_3$ and $R_4$ in the compound of claim 1 are independently selected from phenyl, naphthyl, furyl, pyrrolyl, thienyl, imidazolyl, thiadiazolyl, pyridinyl, pyridazinyl, pyrimidinyl, benzothiazolyl and oxadiazolyl.

14. The pharmaceutical composition of claim 13, wherein the compound is an addition salt of hydrochloride, hydrobromide, phosphate, nitrate, acetate, malate, succinate, fumarate, tartrate, salicylate, sorbate, lactate, p-toluene sulphate, or naphthalene-1,5-disulfonate.

* * * * *